United States Patent
Jaryal et al.

(10) Patent No.: US 9,365,526 B2
(45) Date of Patent: Jun. 14, 2016

(54) PROCESS FOR THE PREPARATION OF DASATINIB AND ITS INTERMEDIATES

(71) Applicant: SUN PHARMACEUTICAL INDUSTRIES LIMITED, Mumbai, Maharashtra (IN)

(72) Inventors: Jagdev Singh Jaryal, Kangra (IN); Munish Kapoor, Amritsar (IN); Swargam Sathyanarayana, Gurgaon (IN); Rajesh Kumar Thaper, Jammu (IN); Mohan Prasad, Haryana (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 14/758,644

(22) PCT Filed: Dec. 31, 2013

(86) PCT No.: PCT/IB2013/061453
§ 371 (c)(1),
(2) Date: Jun. 30, 2015

(87) PCT Pub. No.: WO2014/102759
PCT Pub. Date: Jul. 3, 2014

(65) Prior Publication Data
US 2015/0336913 A1 Nov. 26, 2015

(30) Foreign Application Priority Data
Dec. 31, 2012 (IN) .......................... 4048/DEL/2012

(51) Int. Cl.
C07D 277/56 (2006.01)
C07D 417/12 (2006.01)

(52) U.S. Cl.
CPC ............ *C07D 277/56* (2013.01); *C07D 417/12* (2013.01)

(58) Field of Classification Search
CPC .......................... C07D 227/56; C07D 417/12
See application file for complete search history.

(56) References Cited

U.S. PATENT DOCUMENTS

| | | | |
|---|---|---|---|
| 6,596,746 B1 | 7/2003 | Das et al. | 514/370 |
| 7,189,854 B2 * | 3/2007 | Das | C07C 237/40 546/270.1 |
| 7,491,725 B2 | 2/2009 | Lajeunesse et al. | 514/252.19 |
| 8,993,567 B2 * | 3/2015 | Das | C07C 237/40 514/235.8 |
| 2005/0261305 A1 | 11/2005 | Das et al. | 514/252.19 |
| 2006/0004067 A1 | 1/2006 | Chen et al. | 514/370 |

FOREIGN PATENT DOCUMENTS

| WO | WO 2005/077945 | 8/2005 | ........... C07D 277/56 |
|---|---|---|---|
| WO | WO 2007/019210 | 2/2007 | ........... C07D 277/56 |
| WO | WO 2007/106879 | 9/2007 | ........... C07D 277/56 |
| WO | WO 2008/076883 | 6/2008 | ........... A61K 31/675 |
| WO | WO 2010/144338 | 12/2010 | ............ A01N 43/66 |
| WO | WO 2011/095125 | 8/2011 | ........... C07D 417/14 |

OTHER PUBLICATIONS

Lombardo et al., "Discovery of N-(2-Chloro-6-methyl-methyl-phenyl)-2-(6-(4-(2-hydroxyethyl)-piperazin-l-yl)-2-methylpyrimidin-4-ylamino)thiazole-5-carboxamide (BMS-354825), a Dual Src/Abl Kinase Inhibitor with Potent Antitumor Activity in Preclinical Assays," *Journal of Medicinal Chemistry*, 47(27):6658-6661 (2004).

Chen et al., "A new and efficient preparation of 2-aminothiazole-5-carbamides: applications to the synthesis of the anti-cancer drug dasatinib," *ARKIVOC*, 2010(vi):32-38 (2010).

Das et al., "2-Aminothiazole as a Novel Kinase Inhibitor Template. Structure-Activity Relationship Studies toward the Discovery of N-(2-Chloro-6-methylphenyl)-2-[[6-[-[4-(2-hydroxyethyl)-1-piperazinyl]-2-methyl-4-pyrimidinyl]amino)]-1,3-thiazole-5-carboxamide (Dasatinib, BMS-354825) as a Potent *pan*-Src Kinase Inhibitor," *Journal of Medicinal Chemistry*, 49(23):6819-6832 (2006).

Muñoz et al., "Preparation of amides mediated by isopropylmagnesium chloride under continuous flow conditions," *Green Chemistry*, 14(5):1335-1341 (2012).

Hou et al., "Manufacture of dasatinib involves acyl chlorinating chlorine-containing compound, reacting obtained compound with 2-chloro-6-methylaniline, and reacting resultant compound with 1-(2-hydroxyethyl)piperazine" (2011) Database WPI Abstract of WO 2011/095125 (Patent in Chinese).

Wang, 2010. Chapter 96—Bodroux Amide Synthesis. In *Comprehensive Organic Name Reactions and Reagents*. Hoboken, NJ: John Wiley & Sons, Inc., pp. 445-447.

* cited by examiner

*Primary Examiner* — Golam M M Shameem

(57) ABSTRACT

The present invention relates to processes for the preparation of dasatinib and its intermediates.

5 Claims, No Drawings

PROCESS FOR THE PREPARATION OF DASATINIB AND ITS INTERMEDIATES

FIELD OF THE INVENTION

The present invention relates to processes for the preparation of dasatinib and its intermediates.

BACKGROUND OF THE INVENTION

Dasatinib monohydrate of Formula A, chemically, N-(2-chloro-6-methylphenyl)-2-[[6-[4-(2-hydroxyethyl)-1-piperazinyl]-2-methyl-4-pyrimidinyl]amino]-5-thiazolecarboxamide monohydrate, is a cyclic protein tyrosine kinase inhibitor. Dasatinib monohydrate is marketed under the brand name SPRYCEL® and is indicated for the treatment of adults with chronic, accelerated, or myeloid or lymphoid blast phase Philadelphia chromosome-positive chronic myeloid leukemia (Ph+ CML) with resistance or intolerance to prior therapy including imatinib. SPRYCEL® is also indicated for the treatment of adults with Philadelphia chromosome-positive acute lymphoblastic leukemia (Ph+ ALL) with resistance or intolerance to prior therapy.

Formula A

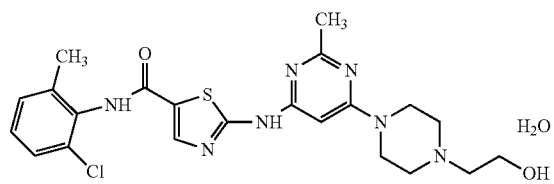

The compound of Formula 1a,

Formula 1a

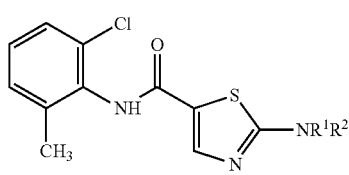

wherein $R^1$ and $R^2$ can be independently selected from the group consisting of hydrogen, amino protecting group, and 6-chloro-2-methyl-pyrimidin-4-yl, 6-[4-(2-hydroxyethyl)-1-piperazinyl]-2-methyl-4-pyrimidinyl, encompasses dasatinib of Formula B, Formula B

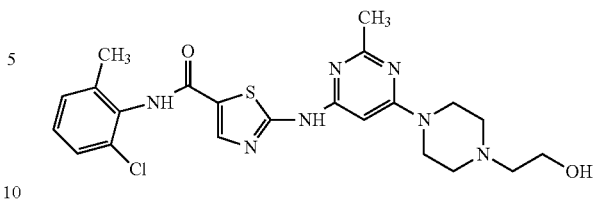

and key intermediates of dasatinib of Formula 1b, Formula 1c, and Formula 1d, or salts thereof Formula 1b

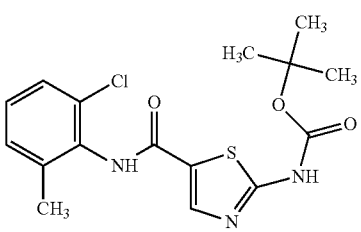

Formula 1c

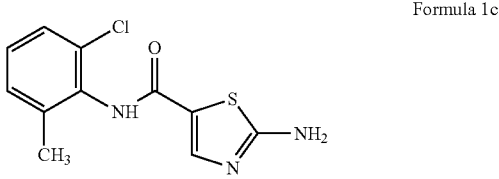 [SMILES: Cc1cccc(Cl)c1NC(=O)c1cnc(N)s1]

Formula 1d

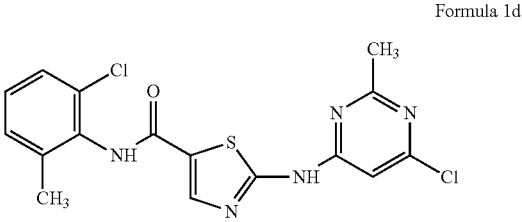 [SMILES: Cc1nc(Cl)cc(Nc2ncc(C(=O)Nc3c(C)cccc3Cl)s2)n1]

U.S. Pat. No. 6,596,746 provides a process for the preparation of tert-butyl {5-[(2-chloro-6-methylphenyl)carbamoyl]-1,3-thiazol-2-yl}carbamate (Formula 1b), 2-amino-N-(2-chloro-6-methylphenyl)-1,3-thiazole-5-carboxamide (Formula 1c), and N-(2-chloro-6-methylphenyl)-2-[(6-chloro-2-methylpyrimidin-4-yl)amino]-1,3-thiazole-5-carboxamide (Formula 1d) which are the intermediates for the preparation of dasatinib.

The process provided in the '746 patent for the preparation of tert-butyl {5-[(2-chloro-6-methylphenyl)carbamoyl]-1,3-thiazol-2-yl}carbamate (Formula 1b), 2-amino-N-(2-chloro-6-methylphenyl)-1,3-thiazole-5-carboxamide (Formula 1c), and N-(2-chloro-6-methylphenyl)-2-[(6-chloro-2-methylpyrimidin-4-yl)amino]-1,3-thiazole-5-carboxamide (Formula 1d) involves four, five, and six synthetic steps, respectively, starting from ethyl 2-amino-1,3-thiazole-5-carboxylate as depicted in the chemical scheme below:

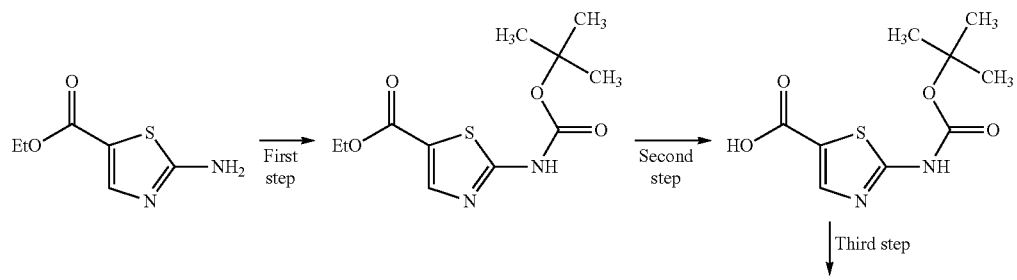

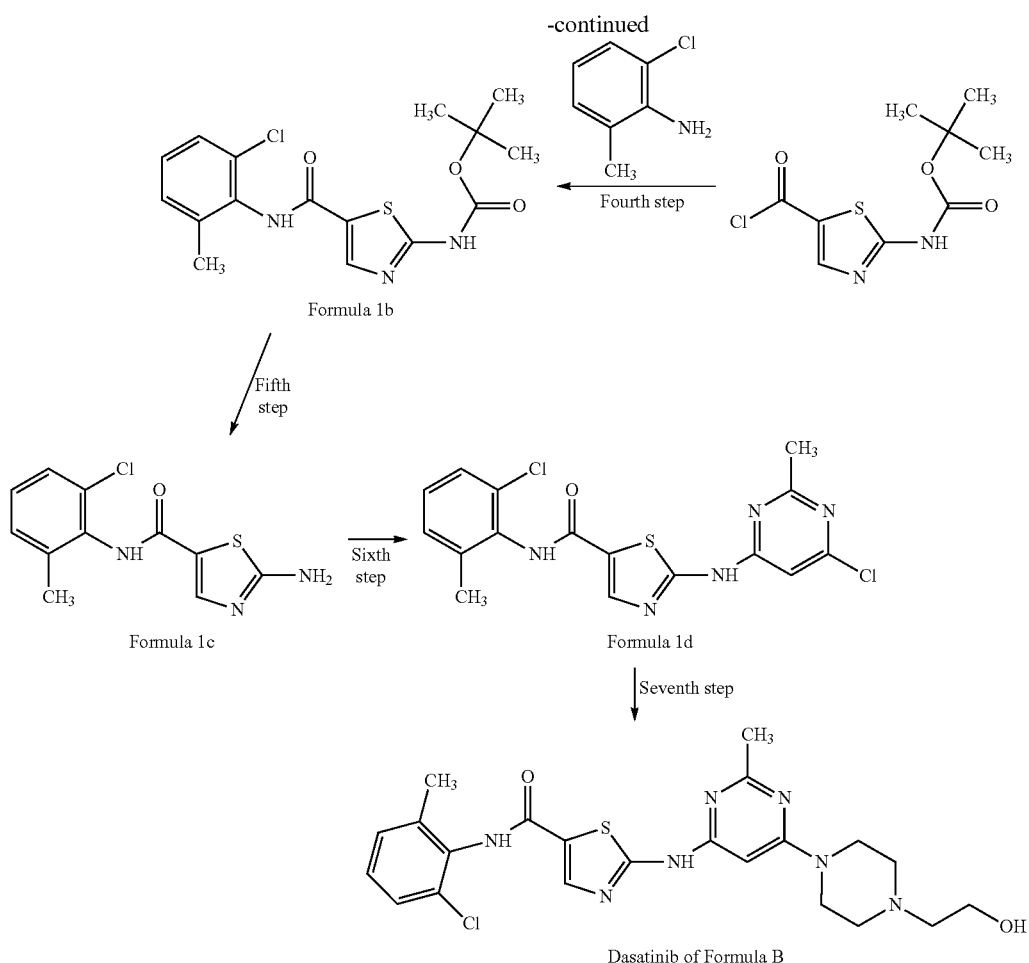

The first step of the process involves stirring a suspension of ethyl 2-amino-1,3-thiazole-5-carboxylate, 4-dimethylaminopyridine, and di-tert-butyl dicarbonate in dry tetrahydrofuran for a time period of 24 hours. The solvent was evaporated in vacuo and the residue obtained was suspended in ether, washed with ether, and dried in vacuo to obtain ethyl 2-[(tert-butoxycarbonyl)amino]-1,3-thiazole-5-carboxylate.

The second step involves treating a stirred solution of ethyl 2-[(tert-butoxycarbonyl)amino]-1,3-thiazole-5-carboxylate in tetrahydrofuran-methanol with 6N aqueous sodium hydroxide solution at room temperature for 24 hours. Most of the tetrahydrofuran-methanol were removed by distillation under reduced pressure and the aqueous solution was acidified with 6N hydrochloric acid to obtain a solid which was filtered, washed with water and ether, then air dried, followed by drying in vacuo to obtain 2-[(tert-butoxycarbonyl)amino]-1,3-thiazole-5-carboxylic acid.

The third step involves adding a 2M solution of oxalyl chloride in dichloromethane to a stirred solution of 2-[(tert-butoxycarbonyl)amino]-1,3-thiazole-5-carboxylic acid in tetrahydrofuran and N,N-dimethylformamide, and then stirring the solution at room temperature for 4 hours. The solvent was evaporated under reduced pressure and in vacuo to obtain tert-butyl[5-(chlorocarbonyl)-1,3-thiazol-2-yl]carbamate.

The fourth step involves adding 2-chloro-6-methylaniline to a stirred solution of tert-butyl[5-(chlorocarbonyl)-1,3-thiazol-2-yl]carbamate in dichloromethane at 0° C. Diisopropylamine was added to the reaction mixture, warmed to room temperature, stirred for 24 hours, diluted with dichloromethane, and washed with 2N hydrochloric acid. The organic extract thus obtained was dried, filtered, and concentrated to obtain a residue. The residue was diluted with ethyl acetate-ether, filtered, washed with ether, and dried in vacuo to obtain tert-butyl{5-[(2-chloro-6-methylphenyl)carbamoyl]-1,3-thiazol-2-yl}carbamate (Formula 1b) in an overall yield of 48%.

The fifth step involves treating tert-butyl{5-[(2-chloro-6-methylphenyl)carbamoyl]-1,3-thiazol-2-yl}carbamate (Formula 1b) obtained in the fourth step with trifluoroacetic acid at room temperature to obtain 2-amino-N-(2-chloro-6-methylphenyl)-1,3-thiazole-5-carboxamide (Formula 1c).

The sixth step involves reacting 2-amino-N-(2-chloro-6-methylphenyl)-1,3-thiazole-5-carboxamide (Formula 1c) with 4,6-dichloro-2-methylpyrimidine in the presence of sodium hydride in tetrahydrofuran to obtain N-(2-chloro-6-methylphenyl)-2-[(6-chloro-2-methylpyrimidin-4-yl)amino]-1,3-thiazole-5-carboxamide (Formula 1d).

The seventh step of the process involves reacting N-(2-chloro-6-methylphenyl)-2-[(6-chloro-2-methylpyrimidin-4-yl)amino]-1,3-thiazole-5-carboxamide (Formula 1d) obtained in the sixth step with 1-(2-hydroxyethyl)piperazine to obtain dasatinib of Formula B.

*J. Med. Chem.*, 47(27), 6658-6661 (2004), provides a four step process for the preparation of N-(2-chloro-6-methylphenyl)-2-[(6-chloro-2-methylpyrimidin-4-yl)amino]-1,3-thiazole-5-carboxamide (Formula 1d) from 2-chlorothiazole.

The first step of the process involves reacting 2-chlorothiazole with 2-chloro-6-methylphenylisocyanate in the presence of n-butyl lithium in tetrahydrofuran to obtain 2-chloro-N-(2-chloro-6-methylphenyl)-1,3-thiazole-5-carboxamide. The second step involves reacting 2-chloro-N-(2-chloro-6-methylphenyl)-1,3-thiazole-5-carboxamide with 4-methoxybenzylchloride in the presence of sodium hydride in tetrahydrofuran to obtain 2-chloro-N-(2-chloro-6-methylphenyl)-N-(4-methoxybenzyl)-1,3-thiazole-5-carboxamide. The third step involves reacting 2-chloro-N-(2-chloro-6-methylphenyl)-N-(4-methoxybenzyl)-1,3-thiazole-5-carboxamide with 4-amino-6-chloro-2-methylpyrimidine in the presence of sodium hydride in tetrahydrofuran at reflux temperature to obtain N-(2-chloro-6-methylphenyl)-2-[(6-chloro-2-methylpyrimidin-4-yl)amino]-N-(4-methoxybenzyl)-1,3-thiazole-5-carboxamide. The fourth step involves reacting N-(2-chloro-6-methylphenyl)-2-[(6-chloro-2-methylpyrimidin-4-yl)amino]-N-(4-methoxybenzyl)-1,3-thiazole-5-carboxamide with trifluoromethanesulfonic acid and trifluoroacetic acid in dichloromethane to obtain N-(2-chloro-6-methylphenyl)-2-[(6-chloro-2-methylpyrimidin-4-yl)amino]-1,3-thiazole-5-carboxamide (Formula 1d).

PCT Publication No. WO 2005/077945 provides a process for the preparation of 2-amino-N-(2-chloro-6-methylphenyl)-1,3-thiazole-5-carboxamide (Formula 1c) which involves adding 3-ethoxyacryloyl chloride to a cold stirring solution of 2-chloro-6-methylaniline and pyridine in tetrahydrofuran at a temperature of 0° C. to 5° C. The mixture thus obtained was then warmed, stirred for 2 hours at 20° C., and hydrochloric acid was added at 0° C. to 10° C. The mixture was diluted with water and the resulting solution was concentrated under vacuum to a thick slurry. The slurry was diluted with toluene and stirred for 15 minutes at 20° C. to 22° C. then for 1 hour at 0° C. to obtain (E)-N-(2-chloro-6-methylphenyl)-3-ethoxyacrylamide.

N-Bromosuccinamide was added to a mixture of (E)-N-(2-chloro-6-methylphenyl)-3-ethoxyacrylamide in 1,4-dioxane and water at −10° C. to 0° C. to obtain a slurry which was warmed and stirred at 20° C. to 22° C. for 3 hours. Thiourea was added and the mixture was heated to 80° C. After 2 hours, the resulting solution was cooled to 20° C. to 22° C. and concentrated ammonium hydroxide was added dropwise. The resulting slurry was concentrated under vacuum to about half volume and cooled to 0° C. to 5° C. to obtain a solid which was collected by vacuum filtration, washed with cold water, and dried to obtain 2-amino-N-(2-chloro-6-methylphenyl)thiazole-5-carboxamide (Formula 1c).

Several processes are known in the literature for the preparation of 2-amino-N-(2-chloro-6-methylphenyl)-1,3-thiazole-5-carboxamide (Formula 1c), for example, PCT Publication Nos. WO 2007/019210, WO 2007/106879, WO 2008/076883, and WO 2010/144338.

Several processes are known in the literature for the preparation of N-(2-chloro-6-methylphenyl)-2-[(6-chloro-2-methylpyrimidin-4-yl)amino]-1,3-thiazole-5-carboxamide (Formula 1d), for example, U.S. Publication No. US 2006/0004067; PCT Publication Nos. WO 2007/106879 and WO 2011/095125; *ARKIVOC*, 2010(6), 32-38 (2010); and *J. Med. Chem.*, 49(23), 6819-6832 (2006).

The processes described in the prior art for the preparation of tert-butyl{5-[(2-chloro-6-methylphenyl)carbamoyl]-1,3-thiazol-2-yl}carbamate (Formula 1b), 2-amino-N-(2-chloro-6-methylphenyl)-1,3-thiazole-5-carboxamide (Formula 1c), and N-(2-chloro-6-methylphenyl)-2-[(6-chloro-2-methylpyrimidin-4-yl)amino]-1,3-thiazole-5-carboxamide (Formula 1d) suffer from one or more disadvantages such as a low yield, high number of chemical reaction steps, difficulties in isolation of the products, and usage of hazardous reagents such as oxalyl chloride, thionyl chloride, n-butyl lithium, and N-bromosuccinamide. Therefore, processes described in the prior art for the preparation of tert-butyl {5-[(2-chloro-6-methylphenyl)carbamoyl]-1,3-thiazol-2-yl}carbamate (Formula 1b), 2-amino-N-(2-chloro-6-methylphenyl)-1,3-thiazole-5-carboxamide (Formula 1c), and N-(2-chloro-6-methylphenyl)-2-[(6-chloro-2-methylpyrimidin-4-yl)amino]-1,3-thiazole-5-carboxamide (Formula 1d) are believed to be unsuitable and/or undesirable for commercial scale production.

SUMMARY OF THE INVENTION

The present inventors have found an improved process for the preparation of the compound of Formula 1a by directly reacting the compound of Formula 2a with an activated derivative of 2-chloro-6-methylaniline produced in situ by treating 2-chloro-6-methylaniline with ethylmagnesium bromide. The present invention does not involve the use of a hazardous reagent such as oxalyl chloride, thionyl chloride, n-butyl lithium, or N-bromosuccinamide.

Thus, the present invention provides an efficient, industrially preferable, and economic process for the preparation of compound of Formula 1a in good yield with excellent chemical purity and a reduced number of process steps. The present invention avoids the excess usage of environmentally hazardous reagents and organic solvents, thereby promoting green chemistry and ensuring a cleaner surrounding by putting a reduced load on the environment.

DETAILED DESCRIPTION OF THE INVENTION

The term "amino protecting group", as used herein, refers to a chemical group that prevents an otherwise reactive amino group from participating in undesirable chemical reactions and which may be subsequently removed easily during the process steps when protection of the reactive amino group is no longer required. Examples of amino protecting groups include, but are not limited to, acyl groups such as acetyl, trifluoroacetyl, benzoyl, and the like; alkoxycarbonyl groups such tert-butyloxycarbonyl (BOC); aryl-lower alkoxycarbonyl such as benzyloxycarbonyl; trityl; and 9-fluorenylmethoxycarbonyl.

The term "combining" includes adding, dissolving, slurrying, stirring, or a combination thereof.

The term "solvent", as used herein, refers to any solvent or solvent mixtures, including, for example, water, aromatic hydrocarbons, esters, halogenated hydrocarbons, ketones, ethers, polar aprotic solvents, or mixtures thereof. Examples of aromatic hydrocarbons include toluene and xylene. Examples of esters include ethyl acetate, n-propyl acetate, isopropyl acetate, and n-butyl acetate. Examples of halogenated hydrocarbons include dichloromethane, chloroform, and 1,2-dichloroethane Examples of ketones include acetone and methyl ethyl ketone. Examples of ethers include diethyl ether and tetrahydrofuran. Examples of polar aprotic solvents include N,N-dimethylformamide, N,N-dimethylacetamide, dimethylsulphoxide, acetonitrile, and N-methylpyrrolidone.

A first aspect of the present invention provides a process for the preparation of compound of Formula 1a or a salt thereof Formula 1a

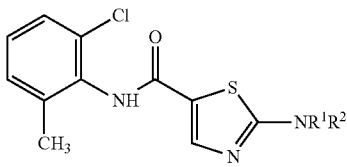

which comprises, reacting a compound of Formula 2a or a salt thereof with a compound of Formula 3, Formula 2a

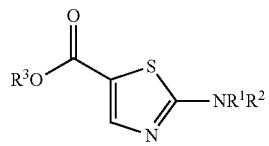

Formula 3

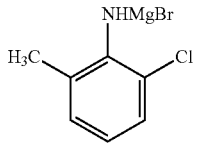

wherein $R^1$ and $R^2$ can be independently selected from the group consisting of hydrogen, amino protecting group, 6-chloro-2-methyl-pyrimidin-4-yl, and 6-[4-(2-hydroxyethyl)-1-piperazinyl]-2-methyl-4-pyrimidinyl; and $R^3$ can be independently selected from the group consisting of $C_1$-$C_6$ alkyl, $C_6$-$C_{12}$ aryl, $C_7$-$C_{12}$ arylalkyl, and $C_7$-$C_{12}$ alkylaryl.

Reacting a compound of Formula 2a or a salt thereof with a compound of Formula 3 comprises combining a compound of Formula 2a or a salt thereof with a compound of Formula 3.

Reacting a compound of Formula 2a or a salt thereof with a compound of Formula 3 may be performed in one or more solvents at a temperature of about 15° C. to about 40° C. for a time period sufficient to complete the reaction.

The compound of Formula 3 of the present invention may be prepared in situ by combining 2-chloro-6-methylaniline with ethylmagnesium bromide in one or more solvents at a temperature of −10° C. to 10° C. for a time period sufficient to complete the reaction.

After the completion of the reaction, the compound of Formula 1a can be isolated by a common isolation technique such as cooling, extraction, washing, crystallization, precipitation, filtration, filtration under vacuum, decantation, centrifugation, or a combination thereof.

The isolated compound of Formula 1a may be purified by crystallization from solvents, chromatographic methods, or a combination thereof.

A second aspect of the present invention provides a process for the preparation of compound of Formula 1b or a salt thereof Formula 1b

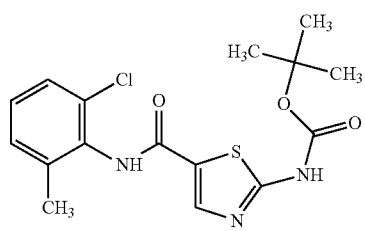

which comprises reacting a compound of Formula 2b or a salt thereof with a compound of Formula 3, Formula 2b

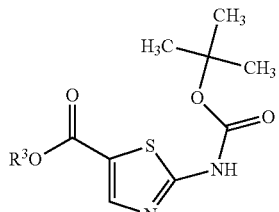

Formula 3

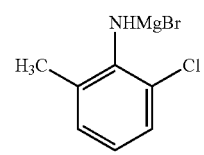

wherein $R^3$ can be independently selected from the group consisting of $C_1$-$C_6$ alkyl, $C_6$-$C_{12}$ aryl, $C_7$-$C_{12}$ arylalkyl, and $C_7$-$C_{12}$ alkylaryl.

Reacting a compound of Formula 2b or a salt thereof with a compound of Formula 3 comprises combining a compound of Formula 2b or a salt thereof with a compound of Formula 3.

Reacting a compound of Formula 2b or a salt thereof with a compound of Formula 3 may be performed in one or more solvents at a temperature of about 15° C. to about 40° C. for a time period sufficient to complete the reaction.

The compound of Formula 3 of the present invention may be prepared in situ by combining 2-chloro-6-methylaniline with ethylmagnesium bromide in one or more solvents at a temperature of −10° C. to 10° C. for a time period sufficient to complete the reaction.

After the completion of the reaction, the compound of Formula 1b can be isolated by a common isolation technique such as cooling, extraction, washing, crystallization, precipitation, filtration, filtration under vacuum, decantation, centrifugation, or a combination thereof.

The isolated compound of Formula 1b may be purified by crystallization from solvents, chromatographic methods, or a combination thereof.

The compound of Formula 1b is a suitable intermediate for the preparation of dasatinib or a pharmaceutically acceptable salt, solvate, or hydrate thereof.

A third aspect of the present invention provides a process for the preparation of compound of Formula 1c or a salt thereof Formula 1c

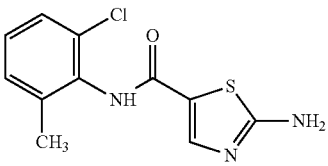

which comprises reacting a compound of Formula 2c or a salt thereof with a compound of Formula 3,

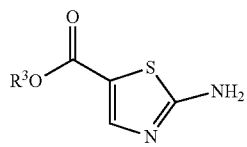
Formula 2c

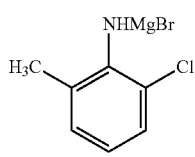
Formula 3 wherein $R^3$ can be independently selected from the group consisting of $C_1$-$C_6$ alkyl, $C_6$-$C_{12}$ aryl, $C_7$-$C_{12}$ arylalkyl, and $C_7$-$C_{12}$ alkylaryl.

Reacting a compound of Formula 2c or a salt thereof with a compound of Formula 3 comprises combining a compound of Formula 2c or a salt thereof with a compound of Formula 3.

Reacting a compound of Formula 2c or a salt thereof with a compound of Formula 3 may be performed in one or more solvents at a temperature of about 15° C. to about 40° C. for a time period sufficient to complete the reaction.

The compound of Formula 3 of the present invention may be prepared in situ by combining 2-chloro-6-methylaniline with ethylmagnesium bromide in one or more solvents at a temperature of −10° C. to 10° C. for a time period sufficient to complete the reaction.

After the completion of the reaction, the compound of Formula 1c can be isolated by a common isolation technique such as cooling, extraction, washing, crystallization, precipitation, filtration, filtration under vacuum, decantation, centrifugation, or a combination thereof.

The isolated compound of Formula 1c may be purified by crystallization from solvents, chromatographic methods, or a combination thereof.

The compound of Formula 1c is a suitable intermediate for the preparation of dasatinib or a pharmaceutically acceptable salt, solvate, or hydrate thereof.

A fourth aspect of the present invention provides a process for the preparation of compound of Formula 1d or a salt thereof

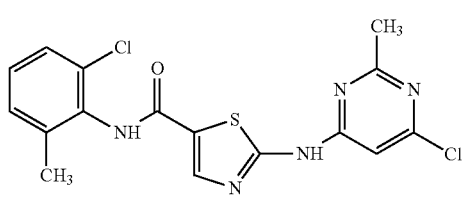
Formula 1d which comprises reacting a compound of Formula 2d or a salt thereof with a compound of Formula 3,

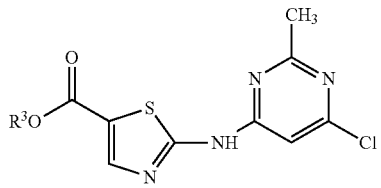
Formula 2d

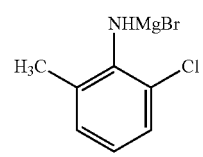
Formula 3 wherein $R^3$ can be independently selected from the group consisting of $C_1$-$C_6$ alkyl, $C_6$-$C_{12}$ aryl, $C_7$-$C_{12}$ arylalkyl, and $C_7$-$C_{12}$ alkylaryl.

Reacting a compound of Formula 2d or a salt thereof with a compound of Formula 3 comprises combining a compound of Formula 2d or a salt thereof with a compound of Formula 3.

Reacting a compound of Formula 2d or a salt thereof with a compound of Formula 3 may be performed in one or more solvents at a temperature of about 15° C. to about 40° C. for a time period sufficient to complete the reaction.

The compound of Formula 3 of the present invention may be prepared in situ by combining 2-chloro-6-methylaniline with ethylmagnesium bromide in one or more solvents at a temperature of −10° C. to 10° C. for a time period sufficient to complete the reaction.

After the completion of the reaction, the compound of Formula 1d can be isolated by a common isolation technique such as cooling, extraction, washing, crystallization, precipitation, filtration, filtration under vacuum, decantation, centrifugation, or a combination thereof.

The isolated compound of Formula 1d may be purified by crystallization from solvents, chromatographic methods, or a combination thereof.

The compound of Formula 1d is a suitable intermediate for the preparation of dasatinib or a pharmaceutically acceptable salt, solvate, or hydrate thereof.

A fifth aspect of the present invention provides a process for the purification of tert-butyl {5-[(2-chloro-6-methylphenyl)carbamoyl]-1,3-thiazol-2-yl}carbamate of Formula 1b or a salt thereof

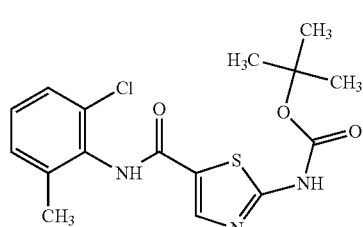
Formula 1b comprising the steps of:
  a) providing a mixture of tert-butyl{5-[(2-chloro-6-methylphenyl)carbamoyl]-1,3-thiazol-2-yl}carbamate of Formula 1b or a salt thereof and aqueous methanol; and
  b) isolating tert-butyl{5-[(2-chloro-6-methylphenyl)carbamoyl]-1,3-thiazol-2-yl}carbamate of Formula 1b or a salt thereof.

Step a) includes combining tert-butyl {5-[(2-chloro-6-methylphenyl)carbamoyl]-1,3-thiazol-2-yl}carbamate of Formula 1b or a salt thereof with aqueous methanol.

The ratio of methanol and water in aqueous methanol may be about 1:1.

The volume of aqueous methanol may be about 2 times to about 15 times, preferably, 3 times to 10 times, more preferably, 3 times to 6 times more than the weight of tert-butyl {5-[(2-chloro-6-methylphenyl)carbamoyl]-1,3-thiazol-2-yl}carbamate of Formula 1b.

Step b) involves isolating tert-butyl{5-[(2-chloro-6-methylphenyl)carbamoyl]-1,3-thiazol-2-yl}carbamate of Formula 1b or a salt thereof by common isolation techniques such as extraction, crystallization, precipitation, filtration, decantation, centrifugation, or a combination thereof.

A sixth aspect of the present invention provides a process for the preparation of dasatinib of Formula B Formula B

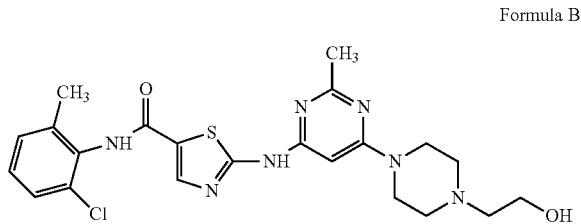 [SMILES: Cc1nc(Nc2ncc(C(=O)Nc3c(C)cccc3Cl)s2)cc(N2CCN(CCO)CC2)n1]

or a pharmaceutically acceptable salt, solvate, or hydrate thereof, comprising the steps of:
a) reacting a compound of Formula 2a or a salt thereof with a compound of Formula 3

Formula 2a

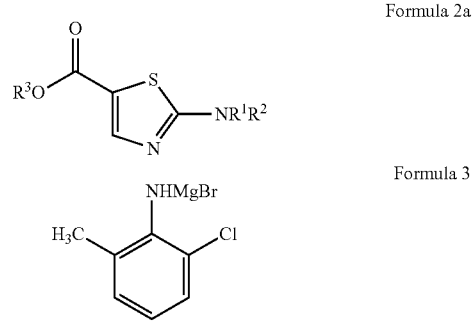

Formula 3 to provide a compound of Formula 1a, or a salt thereof,

Formula 1a

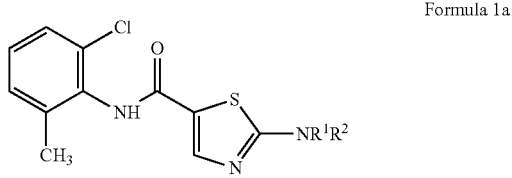

wherein $R^1$ can be selected from hydrogen; $R^2$ can be selected from the group consisting of hydrogen, amino protecting group, 6-chloro-2-methyl-pyrimidin-4-yl, and 6-[4-(2-hydroxyethyl)-1-piperazinyl]-2-methyl-4-pyrimidinyl; and $R^3$ can be independently selected from the group consisting of $C_1$-$C_6$ alkyl, $C_6$-$C_{12}$ aryl, $C_7$-$C_{12}$ arylalkyl, and $C_7$-$C_{12}$ alkylaryl; and b) converting the compound of Formula 1a to dasatinib or a pharmaceutically acceptable salt, solvate, or hydrate thereof when $R^2$ is not 6-[4-(2-hydroxyethyl)-1-piperazinyl]-2-methyl-4-pyrimidinyl.

Step a) of reacting a compound of Formula 2a or a salt thereof with a compound of Formula 3 comprises combining a compound of Formula 2a or a salt thereof with a compound of Formula 3.

Reacting a compound of Formula 2a or a salt thereof with a compound of Formula 3 may be performed in one or more solvents at a temperature of about 15° C. to about 40° C. for a time period sufficient to complete the reaction.

The compound of Formula 3 of the present invention may be prepared in situ by treating 2-chloro-6-methylaniline with ethyl magnesium bromide in one or more solvents at a temperature of −10° C. to 10° C. for a time period sufficient to complete the reaction.

After completion of the reaction, the compound of Formula 1a can be isolated by a common isolation technique such as cooling, extraction, washing, crystallization, precipitation, filtration, filtration under vacuum, decantation, centrifugation, or a combination thereof.

The isolated compound of Formula 1a may be purified by crystallization from solvents, chromatographic methods, or a combination thereof.

In step b), the compound of Formula 1a may be converted to dasatinib or a pharmaceutically acceptable salt, solvate, or hydrate thereof by suitable processes known in the art, for example, as in U.S. Pat. Nos. 6,596,746 and 7,491,725; PCT Publication No. WO 2007/106879; and ARKIVOC 2010(6), 32-38 (2010).

Methods:

Residue on Ignition: Analysis was performed as per the procedure provided as Test 281 "Residue on Ignition", in United States Pharmacopeia 29.

HPLC purity was determined using an Agilent Technologies®, Kromasil C8 (250×4.6 mm), 5 μm column with a flow rate 1.2 mL/min; Column oven temperature 50° C.; Sample oven temperature disable; Detector UV at 285 nm; Injection volume 10 μL; Run time 55 minutes.

While the present invention has been described in terms of its specific embodiments, certain modifications and equivalents will be apparent to those skilled in the art and are intended to be included within the scope of the present invention.

EXAMPLES

Example 1

Preparation of tert-butyl {5-[(2-chloro-6-methylphenyl)carbamoyl]-1,3-thiazol-2-yl}carbamate Magnesium turnings (3.87 g) were charged into a round bottom flask. Tetrahydrofuran (15 mL) was added to the flask. A solution of ethyl bromide (16 g in 60 mL tetrahydrofuran) was prepared and 10 mL of this solution was slowly charged to the round bottom flask. Iodine (30 mg) was added to the reaction mixture and stirred at 25° C. to 32° C. for 5 minutes. The reaction mixture was warmed to 27° C. and the remaining amount of ethyl bromide was added slowly over 30 minutes. The reaction mixture was heated to gentle reflux for 30 minutes and was then cooled to 0° C. 2-Chloro-6-methylaniline (22.86 g) was added drop-wise at 0° C. and the temperature of the reaction mixture was slowly raised to 20° C. to 25° C. Ethyl 2-[(tert-butoxycarbonyl)amino]-1,3-thiazole-5-carboxylate (10 g) dissolved in tetrahydrofuran (60 mL) was slowly added to the reaction mixture over 30 minutes. The reaction mixture was stirred for 3 hours. The reaction mixture was poured slowly into 25% ammonium chloride solution (200 mL) with stirring. Ethyl acetate (200 mL) was added and stirred for 30 minutes, filtered, suck dried, and dried under vacuum at 40° C. to 45° C. to obtain the title compound.

Yield: 10.22 g

Example 2

Preparation of tert-Butyl {5-[(2-chloro-6-methylphenyl)carbamoyl]-1,3-thiazol-2-yl}carbamate Magnesium turnings (3.87 g) were charged into a round bottom flask. Tetrahydrofuran (15 mL) was added to the flask. Iodine (30 mg) was added. A solution of ethyl bromide (16 g in 60 mL tetrahydrofuran) was prepared and 10 mL of this solution was slowly charged to the round bottom flask. The reaction mixture was stirred at 20° C. to 25° C. for 5 minutes and the remaining amount of ethyl bromide was added slowly over 30 minutes. The reaction mixture was heated to gentle reflux for 30 minutes and was cooled to −5° C. to −10° C. 2-Chloro-6-methylaniline (22.86 g) was added drop-wise at −5° C. to −10° C. and the temperature of the reaction mixture was slowly raised to 15° C. to 20° C. Ethyl 2-[(tert-butoxycarbonyl)amino]-1,3-thiazole-5-carboxylate (10 g) dissolved in tetrahydrofuran (60 mL) was slowly added to the reaction mixture over 30 minutes. The reaction mixture was stirred for 3 hours. The reaction mixture was poured slowly into 25% ammonium chloride solution (100 mL) with stirring. Ethyl acetate (100 mL) was added and stirred for 30 minutes, filtered, suck dried, and dried under vacuum at 40° C. to 45° C. to obtain the title compound.

Yield: 13.00 g
Residue on Ignition: 3.40% w/w

Example 3

Purification of tert-Butyl {5-[(2-chloro-6-methylphenyl)carbamoyl]-1,3-thiazol-2-yl}carbamate tert-Butyl {5-[(2-chloro-6-methylphenyl)carbamoyl]-1,3-thiazol-2-yl}carbamate (10 g) obtained from Example 2 was charged into a round bottom flask and aqueous methanol (1:1, 50 mL) was added to it. The reaction mixture was stirred, filtered, and dried under vacuum at 40° C. to 45° C. for 8 hours to obtain the title compound.

Yield: 9.1 g
HPLC purity: 99.03%

Example 4

Preparation of 2-Amino-N-(2-chloro-6-methylphenyl)-1,3-thiazole-5-carboxamide

Magnesium turnings (12.16 g) were charged into a round bottom flask. Tetrahydrofuran (50 mL) was added to the flask. A solution of ethyl bromide (50.2 g in 200 mL tetrahydrofuran) was prepared and 20 mL of this solution was slowly charged to the round bottom flask. Iodine (30 mg) was added. The reaction mixture was stirred at 20° C. to 22° C. for 10 minutes and the remaining amount of ethyl bromide was added slowly over 30 minutes. The reaction mixture was heated to gentle reflux for 30 minutes and cooled to 0° C. to −10° C. 2-Chloro-6-methylaniline (72.4 g) was added drop-wise at 0° C. and the temperature of the reaction mixture was slowly raised to 20° C. Ethyl 2-amino-1,3-thiazole-5-carboxylate (20 g) dissolved in tetrahydrofuran (200 mL) was slowly added to the reaction mixture over 60 minutes. The reaction mixture was stirred for 3 hours. The progress of the reaction was monitored by thin layer chromatography. The reaction mixture was further stirred for 16 hours and then poured slowly into 25% ammonium chloride solution (200 mL) with stirring. The oily layer was separated, diluted with ethyl acetate (200 mL), and washed with 2 N hydrochloric acid (200 mL). The layers were separated and the pH of the aqueous layer was adjusted to between 8 and 9 with saturated sodium bicarbonate solution (300 ml) and extracted with ethyl acetate (2×100 mL). The oily layer was collected, concentrated, and further purified by column chromatography to obtain the title compound.

Yield: 17.0 g.

The invention claimed is:

1. A process for the preparation of a compound of Formula 1a or a salt thereof

Formula 1a

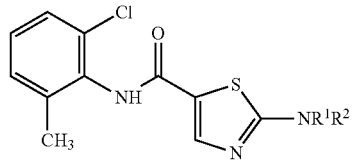

which comprises reacting a compound of Formula 2a or a salt thereof with a compound of Formula 3, Formula 2a

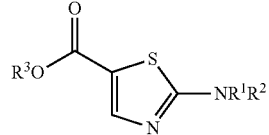

Formula 3

wherein $R^1$ and $R^2$ are independently selected from the group consisting of hydrogen, amino protecting group, 6-chloro-2-methyl-pyrimidin-4-yl, and 6-[4-(2-hydroxyethyl)-1-piperazinyl]-2-methyl-4-pyrimidinyl; and $R^3$ is independently selected from the group consisting of $C_1$-$C_6$ alkyl, $C_6$-$C_{12}$ aryl, $C_7$-$C_{12}$ arylalkyl, and $C_7$-$C_{12}$ alkylaryl.

2. The process according to claim 1, wherein reacting the compound of Formula 2a or a salt thereof with the compound of Formula 3 is performed in one or more solvents at a temperature of 15° C. to 40° C.

3. The process according to claim 1, wherein the compound of Formula 3 is prepared in situ by combining 2-chloro-6-methylaniline with ethyl magnesium bromide in one or more solvents at a temperature of −10° C. to 10° C.

4. The process according to claim 3, wherein the solvent is selected from the group consisting of water, aromatic hydrocarbons, esters, halogenated hydrocarbons, ketones, ethers, polar aprotic solvents, and mixtures thereof.

5. The process according to claim 2, wherein the solvent is selected from the group consisting of water, aromatic hydrocarbons, esters, halogenated hydrocarbons, ketones, ethers, polar aprotic solvents, and mixtures thereof.

* * * * *